United States Patent [19]

Manimaran

[11] Patent Number: 5,302,263

[45] Date of Patent: Apr. 12, 1994

[54] ULTRASONIC CYANO-DE-HALOGENATION

[75] Inventor: Thanikavelu Manimaran, Baton Rouge, La.

[73] Assignee: Ethyl Corporation, Richmond, Va.

[21] Appl. No.: 54,586

[22] Filed: Apr. 29, 1993

[51] Int. Cl.$^5$ .............................. C07B 43/08
[52] U.S. Cl. ........................... 204/157.62; 558/342
[58] Field of Search ................... 558/343; 204/157.62

[56] References Cited

PUBLICATIONS

Rapport, "The Chemistry of the Cyano Group", pp. 77-84, (1970), Intesciences, N.Y., N.Y.

Ley et al., *Ultrasound in Synthesis*, pp. 83-84, Springer-Verlag, New York (1989).

Einhorn et al., *Synthesis: Review*, pp. 787-813, Nov., 1989.

*Primary Examiner*—Joseph Paul Brust
*Attorney, Agent, or Firm*—Richard J. Hammond

[57] ABSTRACT

A process for obtaining an aryl-substituted aliphatic nitrile is described. The process utilizes a solution of an aryl-substituted aliphatic halide and an organic or inorganic cyanide substantially insoluble in the solution. The mixture is subjected to ultrasonic vibrations for a time and at a temperature sufficient to produce the aryl-substituted aliphatic nitrile.

8 Claims, No Drawings

ULTRASONIC CYANO-DE-HALOGENATION

FIELD OF INVENTION

A process is disclosed for the preparation of aryl-substituted aliphatic nitriles by ultrasonic acceleration. Specifically, a benzylic halide is reacted with organic or inorganic cyanide under ultrasonic conditions to produce the corresponding benzylic cyanide.

BACKGROUND OF INVENTION

The reaction between cyanide ions and alkyl halides is a well-known and convenient method for the preparation of nitriles. Primarily, benzylic and alkylic halides are known to give acceptable yields of nitrile when the reaction is carried out under the proper conditions, i.e., using relatively high temperatures and polar solvents. See, for example, Freidrich et al., in Rappoport, "The Chemistry of the Cyano Group", pp. 87-86, Interscience, New York, N.Y., 1970. However, since the cyanide ion is one of the stronger bases, olefin formation (and concurrent dimerizations and polymerizations) are unavoidable.

While a great deal of research has provided numerous examples where ultrasound (sound waves whose frequencies lie within the range of 20 to 10,000 kHz) has been used to activate metal surfaces, the literature does provide a limited number of examples where inorganic bases can be used under heterogeneous conditions in organic reactions.

Shibata et al. have described the cyanomethylation of a variety of chalcones by the Michael addition of the radical anion derived from acetonitrile. Sonolysis for about fifteen minutes in the presence of potassium peroxide produced the desired nitrile. See Shibata et al., Chem. Lett., 519 (1987). Other sonochemical methods permit the use of cyanides of various metals to lengthen the carbon chain by one unit under extremely simple conditions. Acyl cyanide, for example, is readily prepared at low temperatures using potassium cyanide under ultrasonic conditions. Conventional methods require copper, silver or thallium salts. Ando et al., Synthesis, 637 (1983).

There remains a need to develop a method for preparing substantially pure, simple nitriles in a single step with few competing reactions.

OBJECTS OF THE INVENTION

It is an object of the present invention to provide a process for obtaining a substantially pure aryl-substituted aliphatic nitrile in a single step starting with a halogen precursor.

It is a further object of the present invention to obtain such a substantially pure compound by treating a solution of said halogen precursor and an organic or inorganic cyanide with ultrasonic frequencies.

PREFERRED EMBODIMENTS OF THE INVENTION

In the present specification, "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

"cycloalkyl" means cyclic alkyl having 3 to 7 carbon atoms and includes cyclopropyl, cyclobutyl, cyclopentyl, cyclohexyl and cycloheptyl;

"alkyl-substituted cycloalkyl" means the above cycloalkyl group substituted by one or more alkyl group;

"substituted phenyl" or "substituted naphthyl" means phenyl or naphthyl substituted by at least one substituent selected from the group consisting of halo (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halo (or halogen), and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

By the term "alkylthio" means straight or branched chain hydrocarbon thioether groups of six or less carbon atoms, including methylthio, ethylthio, propylthio, 2-propylthio, 2-butylthio, pentylthio, 3-hexylthio, and the like.

The term "thioether" as used herein describes ether groups conventionally employed in the art, preferably those derived from normal chain, branched chain, cyclic and aromatic hydrocarbons. The term "hydrocarbon" defines both substituted and unsubstituted hydrocarbons. These hydrocarbons are optionally substituted with groups such as hydroxy, alkoxy, alkylthio, halo, and the like. Preferably the hydrocarbons contain from 1 to 12 carbon atoms. Typical thioethers thus include alkylthio, dihaloalkylthio, i.e., alkoxyalkylthio, i.e., alkoxymethylthio, alkylthioalkylthio, i.e., alkylthiomethylthio, and the like.

"alkanoyl" means alkanoyl having 2 to 18 carbon atoms and includes, for example, acetyl, propionyl, butyryl, isobutyryl, pivaloyl, valeryl, hexanoyl, octanoyl, lauroyl and stearoyl;

"substituted benzoyl" or "substituted naphthanoyl" means benzoyl or naphthanoyl which is substituted by at least one substituent selected from the group consisting of halogen, amino, nitro, hydroxy, alkyl, alkoxy and haloalkyl on the benzene ring;

"heteroaryl" means 5 to 10 membered mono or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indo;

"substituted heteroaryl" means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus:

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thienoyl, nicotinoyl, isonicotinoyl, pyrazolylcarbonyl, imidazolylcarbonyl, pyrimidinylcarbonyl and benzimidazolylcarbonyl;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and "Alkoxycarbonyl" may be represented, for example, by the formula C(O)O-alkyl. In this formula, "alkyl" represents a straight-chain or branched hydrocarbon radical having 1 to 12 carbon atoms. Lower alkoxycarbonyl having 1 to about 4 carbon atoms in the alkyl part is preferred. Alkoxycarbonyl, having 1 to 4 carbon atoms in the alkyl part, is particularly preferred. Examples which may be mentioned are the following alkoxycarbonyl radicals: methoxycarbonyl, ethoxycarbonyl, propoxycarbonyl, iso-propoxycarbonyl, butoxycarbonyl or isobutoxycarbonyl.

"Aryloxycarbonyl" may be represented, for example, by the formula -C(O)O-aryl. In this formula, "aryl" represents an aromatic radical having 6 to 12 carbon atoms. Examples of such aromatic radicals include: phenoxycarbonyl and naphthyloxycarbonyl.

The present invention embraces any of the racemates and individual optical isomers thereof of the compounds of formula (I) having an achiral carbon atom.

The objective of the present invention is achieved by dissolving an aryl-substituted aliphatic halide in an inert solvent or a mixture of inert solvents. The halide has the following formula:

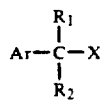

where X is halogen; $R_1$ and $R_2$ are hydrogen, alkyl, cycloalkyl, alkyl-substituted cycloalkyl phenyl, substituted phenyl, naphthyl, substituted naphthyl, alkoxy, alkylthio, heteroaryl either substituted or unsubstituted alkonoyl, benzoyl or naphthanoyl either substituted or unsubstituted, alkoxycarbonyl, aryloxycarbonyl, trifluoromethyl or halo; and Ar is phenyl, substituted phenyl, naphthyl or substituted naphthyl.

Preferred compounds of Formula I are those of the formula:

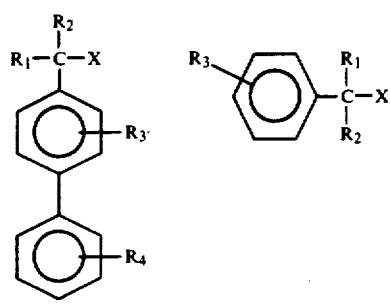

and

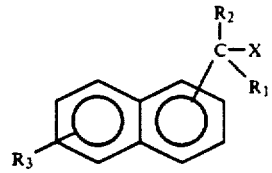

where X, $R_1$, and $R_2$ are as previously defined and $R_3$ and $R_4$ are $C_1$ to $C_4$ linear or branched alkyl, $C_1$ to $C_4$ linear or branched alkoxy or halo.

The process of the present invention is particularly applicable to 1-(4-isobutylphenyl)-1-chloroethane.

The process of the present invention is carried out by treating a compound of formula I with ultrasound in the presence of a solid organic or inorganic cyanide. The process is called sonication. Typically, the sonication is conducted in a heterogeneous anhydrous medium comprised of a liquid medium that is the compound of formula I admixed with the solid cyanide. However, in some cases the compounds of formula I are not mobile liquids but are very viscous liquids. In such cases, it is advantageous to dissolve the compounds of formula I in an inert (anhydrous) solvent, such as a polar solvent. Acceptable solvents are those including dimethylsulfoxide, dimethylformamide, tetrahydrofuran, methylethylketone and ethylalcohol.

Of course, it should be understood that this sonochemical reaction must be carried out in a heterogeneous medium. Thus, should the compounds of formula I be a solid, then the organic or inorganic cyanide should be a liquid or dissolved in an inert solvent that does not dissolve the compound of formula I.

The organic or inorganic cyanides that are of use in the process of the present invention are those that dissociate under ultrasonic conditions to provide the cyanide anion that displaces or replaces the halogen group in the compounds of formula I. While the inorganic metallic cyanides of Group IA or IIA are preferred, e.g., potassium cyanide, sodium cyanide, lithium cyanide, magnesium cyanide, certain other organic cyanides (otherwise known as nitriles) are also useful herein. Cyanogen, benzonitrile or butyl-1-cyanide are illustrative of such organic cyanides.

The process of the present invention utilizing the heterogeneous mixture disclosed above provides compounds of the following formula II

where Ar, $R_1$ and $R_2$ are as previously defined.

The process of the present invention is accomplished by sonication of the reaction mixture of an organic or inorganic cyanide and halo compound of formula I for a time and at a temperature sufficient to produce the compounds of formula II. Those skilled in the art of sonication chemistry readily appreciate these parameters of the reaction. For example, temperatures from about room temperature (25° C.) to about 100° C. are useful in carrying out these reactions with reaction times being from as little as about 15 minutes up to about 24 hours. Preferably the reaction is carried out at about 30° C. to 50° C. for 5 to 15 hours. The presence of a phase transfer agent has, in some cases, been found beneficial to the sonication process, e.g., benzyl triethylammonium bromide.

The product of the reaction is easily separated from the reaction mass by any suitable conventional method, e.g., vacuum distillation, solvent extraction, recrystallization, etc.

The following examples are included herewith for illustrative purposes only. They are not to be regarded as a limitation to the claims setting forth the process of this invention.

EXAMPLES

COMPARATIVE EXAMPLE 1

A solution of 1-chloro-1-(4-isobutylphenyl)ethane (5 mmol) in 10 mL of dimethylformamide was mixed with sodium cyanide (10 mmol) and benzyltriethylammonium chloride (5 mmol), and the suspension was stirred vigorously at 45° C. for 15 hours. GC analysis of the reaction mixture showed only 6% of the expected aralkyl cyanide; it contained more than 70% of the unreacted chloride and 8% of 4-isobutylstyrene.

EXAMPLE 1

General Procedure: A mixture of the α-aralkyl halide (5 mmol), sodium cyanide (10 mmol) and benzyltriethylammonium chloride (5 mmol) in 10 mL of dimethylformamide was taken in a flat vial. The vial was immersed in an ultrasound cleaner filled with water, and sonicated for 15 hours. The reaction mixture was found to contain 75% of the expected aralkyl cyanide and 6% of unreacted halide. The reaction mixture was treated with 25 mL of hexane and filtered. The filtrate was washed with water (2×10 mL) and dried over anhydrous magnesium sulfate. The solvent was removed by evaporation under reduced pressure to isolate the product.

I claim:

1. A process for preparing an aryl-substituted aliphatic nitrile of the following formula II:

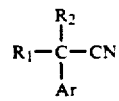

where Ar is phenyl, naphthyl, substituted phenyl or substituted naphthyl and $R_1$ and $R_2$ are hydrogen, alkyl, cycloalkyl, alkyl-unsubstituted, cycloalkyl, phenyl or naphthyl either substituted or unsubstituted, alkoxy, alkylthio, heteroaryl either substituted or unsubstituted, alkanoyl, benzoyl or naphthanoyl either substituted or unsubstituted, heteroarylcarbonyl either substituted or unsubstituted alkoxycarbonyl, aryloxycarbonyl, trifluoromethyl or halo which comprises treating anhydrous solution of a compound of the following formula I

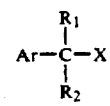

where Ar, $R_1$ and $R_2$ are as previously defined and X is halo with an organic or inorganic cyanide substantially insoluble in said solution at an ultrasonic frequency for a time and at a temperature sufficient to produce said aryl-substituted aliphatic nitrile.

2. The process according to claim 1 wherein said solution is formed from a polar organic solvent.

3. The process according to claim 1 wherein Ar is substituted phenyl or substituted naphthyl and X is chloro or bromo.

4. The process according to claim 3 wherein Ar is phenyl substituted with isobutyl.

5. The process according to claim 1 wherein X is chloro.

6. The process according to claim 1 wherein said compound of formula I is dissolved in an anhydrous polar solvent.

7. The process according to claim 6 wherein said cyanide is an inorganic cyanide.

8. The process of claim 7 wherein said cyanide is sodium cyanide.

* * * * *